United States Patent [19]

Guinta

[11] Patent Number: 4,667,676
[45] Date of Patent: May 26, 1987

[54] METHOD OF EVALUATING THE VESTIBULAR SYSTEM

[75] Inventor: Robert R. Guinta, Woodcliff Lake, N.J.

[73] Assignee: Audimax, Inc., Hackensack, N.J.

[21] Appl. No.: 745,854

[22] Filed: Jun. 17, 1985

[51] Int. Cl.⁴ .............................................. A61N 1/36
[52] U.S. Cl. ................................ 128/419 R; 128/733; 128/791; 128/908
[58] Field of Search ............ 128/419 R, 422, 731–733, 128/741, 791, 905, 908

[56] References Cited

U.S. PATENT DOCUMENTS

| | | | |
|---|---|---|---|
| 3,096,768 | 7/1963 | Griffith, Jr. | 128/422 |
| 3,393,279 | 7/1968 | Flanagan | 128/422 |
| 3,563,246 | 2/1971 | Puharich et al. | 128/422 |
| 3,586,791 | 6/1971 | Puharich et al. | 128/422 |
| 4,249,537 | 2/1981 | Lee et al. | 128/422 |

Primary Examiner—William E. Kamm
Attorney, Agent, or Firm—Brumbaugh, Graves, Donohue & Raymond

[57] ABSTRACT

Vestibular stimulation of a patient is effected by applying to the mastoid area metal, disk-like electrodes covered with insulating material, connected in a series resonant circuit including the electrodes and the body tissues therebetween, energizing the series resonant circuit by an ultrasonic frequency carrier, the frequency of which is determined by the series resonant circuit, and modulating the amplitude of the carrier at a frequency in the range from about 0.1 Hz to about 15 Hz to evoke a nystagmus response. The response is recorded as an indication of the condition of the vestibular system of the patient.

3 Claims, 1 Drawing Figure 4,667,676

METHOD OF EVALUATING THE VESTIBULAR SYSTEM

BACKGROUND OF THE INVENTION

This invention relates to a novel method for evaluating the vestibular system, i.e., those parts of a living body concerned with the maintenance of equilibrium. More particularly, it relates to a method of this general character in which electrical stimulation is employed in a simple and highly effective manner to evoke responses indicative of the condition of the vestibular system.

Computer averaging of on-going micro-electrical activity in the central nervous system has provided a tremendous growth in the field of physiologic evaluation of neurologic systems. The measurement of auditory function, through the use of surface electrodes, has remarkably improved the diagnostic and rehabilitative capabilities of the medical, audiologic and rehabilitation communities in the past fifteen years. As a result, there are a great number of commercially available clinical signal averaging instruments for evoked response measurements in use at this time. Most of these have a multi-modal stimulus capability and are supplemented by programmable and/or dedicated computers and data storage facilities.

One of the sensory pathways, however, the vestibular system, has been relatively neglected due to the lack of a reliable and less traumatic vestibular stimulation apparatus than has been available in the past. The current technique of evaluation of the vestibular system involves, in part, either the irrigation of the ears with cold and hot water for a period of time or moving the patient in a chair. These types of stimulation generate responses which are measured by the resulting reflexive eye movements. The procedures allow for a wide range of errors, cross at least two separate systems (optic/vestibular), are physically uncomfortable and require a degree of patient cooperation.

It is an object of the invention, accordingly, to provide a new and improved method for evaluating the vestibular system that is accurate and reliable, yet can be practiced with minimum discomfort to a patient being tested.

According to the invention, vestibular stimulation is effected by applying to the mastoid area of a patient metal electrodes covered with an insulating material such as Mylar, for example, connected in a series resonant circuit including the electrodes and the body tissues therebetween, energizing the series resonant circuit by an ultrasonic frequency carrier, the frequency of which is determined by the series resonant circuit, and modulating the amplitude of the carrier by a frequency in the range from about 0.1 Hz to about 15 Hz. The applied carrier appears to produce vibrations in the tissues at the frequency of the modulating signal that are essentially received as bone-conduction signals. Those signals evoke vestibular responses similar to those produced in the conventional irrigation or moving chair techniques, i.e., the patient has the same feeling of imbalance but avoids the unpleasantness of the first technique and the cumbersomeness of the second.

DESCRIPTION OF A PREFERRED EMBODIMENT

Figure 1:
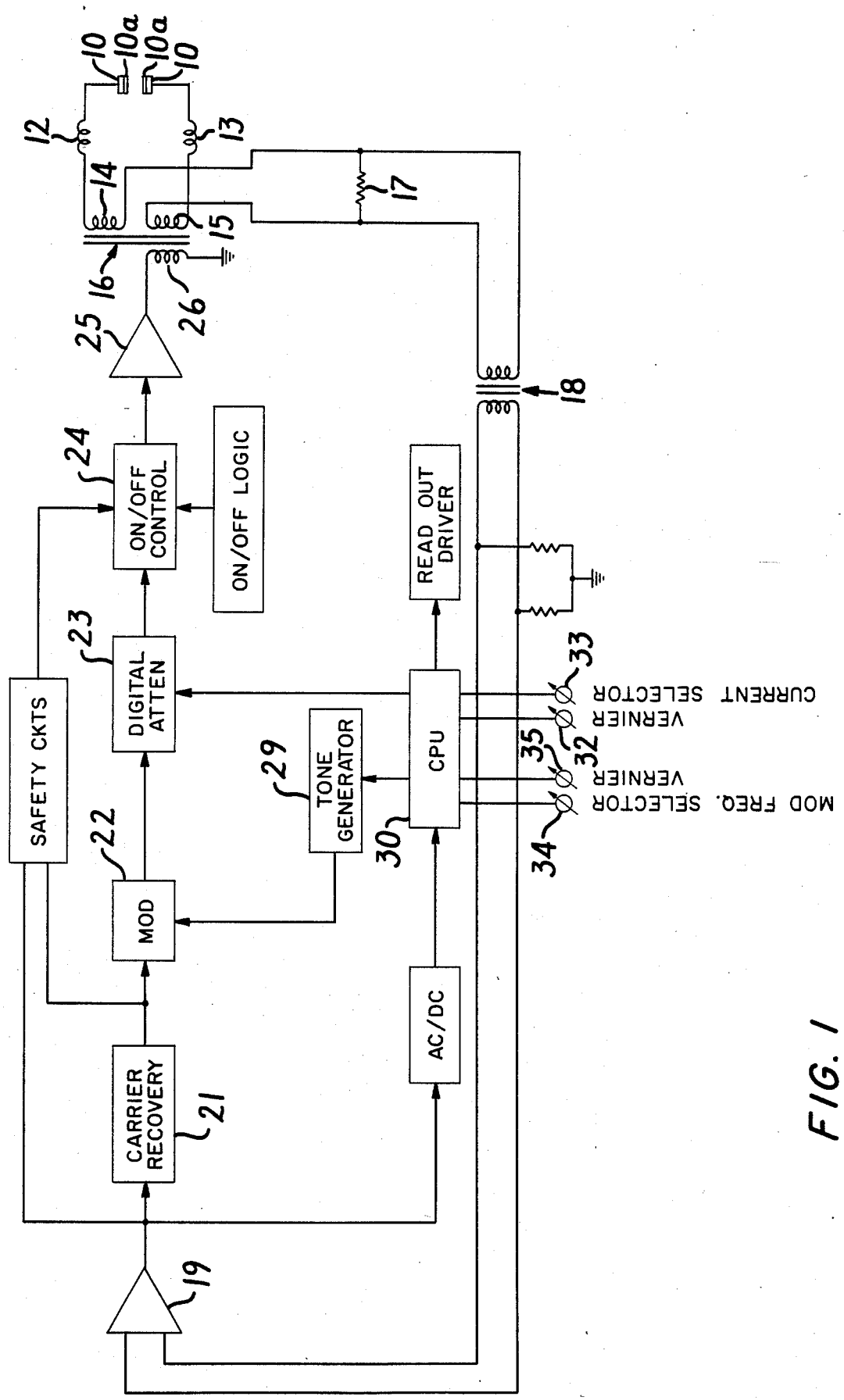

A typical embodiment of the invention is described below and illustrated in the accompanying drawing in which FIG. 1 illustrates schematically stimulator apparatus suitable for practicing the method of the invention.

The practice of the method requires a stimulator apparatus of the capacitive coupling type in which an audio amplitude-modulated, ultrasonic frequency carrier drives a series resonant circuit including electrodes applied to the body of a person to be tested and the tissue impedance therebetween, the frequency of the carrier being determined by the series resonant circuit. Apparatus of the kind described in the copending application Ser. No. 743,509 filed June 11, 1985 by Richard S. Dugot, for AUDIOMETER, is particularly suitable for the purpose. As shown schematically in FIG. 1, it comprises a pair of electrodes 10 for application to the skin of a person to be tested, insulated therefrom by Mylar covers 10a, for example, and connected in a series resonant circuit including two fixed, high Q inductors 12 and 13, the output windings 14 and 15 of an output transformer 16, and a resistor 17.

Since the capacitance of the Mylar-skin interface is one of the elements of the circuit and is variable, the series resonant circuit comprising the Mylar-skin interface and the fixed inductors 12 and 13 is used to determine the frequency of the carrier signal applied to the person to be tested. To this end, the voltage across the resistor 17, which is a measure of the current in the resonant circuit, is fed back positively through a feedback transformer 18 to an input amplifier 19. The amplifier 19 is part of a signal generator including a carrier recovery stage 21, an audio amplitude modulator 22, a digital attenuator 23, an On-Off control 24, and a power amplifier 25, the output of which is fed to the primary winding 26 of the transformer 16. Since the overall feedback is positive, the circuit will maintain oscillation at the frequency determined by the inductors 12 and 13 and the Mylar-skin capacity at the Mylar-covered electrodes 10. The carrier frequency should lie in the range 40-100 KHz, e.g. 60 KHz.

The modulator 22 is connected to receive modulating signals from an audio tone generator 29 described in greater detail below. The carrier recovery and amplitude control circuit 21 serves to strip the modulation off the carrier in the known manner so that the signal entering the modulator 22 consists only of a constant amplitude carrier voltage, which becomes modulated anew each time around. Since the modulating signal is controlled with great precision in the audio tone generator 29, and the amplitude of the carrier supplied from the carrier recovery circuit is constant, the signal at the input to the digital attenuator 23 is constant.

In a typical instrument, the output current supplied to the electrodes 10 may be adjustable over a range of, say, 0.25 ma to 30 ma in 0.25 ma steps. Current magnitude selection is accomplished by generating a digital representation of the output current desired and entering the digital representation into a micro-processor (CPU) 30 where it is compared with a digital representation of the output current to provide a control signal to the digital attenuator to adjust the output current to the desired preset value.

Generation of a digital representation of a desired output is accomplished by presetting manually operable current selectors 32 and 33, the former enabling adjustment of the current in small steps of, say, 0.25 ma and the latter enabling adjustment in larger steps up to a maximum of, say, 30 ma.

The modulating audio frequency similarly is selected by manually settable audio selectors 34 and 35 which are manually adjustable to provide frequency selection over a desired range, the former providing coarse adjustment and the latter fine adjustment. The selectors 34 and 35 supply signals to the CPU 30 which generates therefrom a digital representation of the selected frequency and converts it to an analog value. The analog value is fed to a voltage controlled oscillator in the tone generator 29, causing the latter to generate an audio signal precisely at the preset frequency.

In the practice of the method according to the invention, one of the Mylar-covered electrodes 10 is placed on a mastoid of the person being tested and the other on the other mastoid or on another part of the body such as the arm, for example. Then the current is set at a value between 0.25 ma and 30 ma RMS, a modulation frequency in the range from about 0.1 Hz, say about 10 Hz to about 15 Hz is selected, and the modulated carrier is applied to the series resonant circuit for a short period of time. This generates responses in the form of reflexive eye movements in the patient which can be recorded in the usual manner as by a nystagmograph, for example.

It will be understood that the method according to the invention is ideally suited for vestibular stimulation. By applying to the mastoid area a high frequency carrier modulated at a low frequency in the range from about 0.1 Hz to about 15 Hz, vestibular responses are evoked that are entirely similar to those produced by the conventional irrigation or moving chair methods but without the disadvantages of the latter.

It will be appreciated that the invention is not limited to the specific embodiment described above. Modifications are possible within the scope of the following claims.

I claim:

1. In a method for stimulating the vestibular system of a test subject, the steps of applying an electrode insulated with a layer of dielectric material to the mastoid area of a subject to be tested and another electrode insulated with a layer of dielectric material to the skin on another part of the subject to be tested, forming a series resonant circuit including said electrodes and the tissues therebetween, generating a high frequency carrier, modulating the amplitude of said carrier at a frequency in the range from about 0.1 Hz to about 15 Hz; and energizing said series resonant circuit by said modulated carrier to evoke characteristic responses in the form of reflexive eye movements in the subject representative of the condition of the vestibular system.

2. In a method for stimulating the vestibular system as in claim 1, modulating the amplitude of the carrier at a frequency of about 10 Hz.

3. In a method for stimulating the vestibular system as in claim 2, energizing the series resonant circuit by a high frequency carrier current in the range from about 0.25 ma to 30 ma RMS.

* * * * *

UNITED STATES PATENT AND TRADEMARK OFFICE
CERTIFICATE OF CORRECTION

PATENT NO. : 4,667,676
DATED : May 26, 1987
INVENTOR(S) : Robert R. Guinta

It is certified that error appears in the above—identified patent and that said Letters Patent is hereby corrected as shown below:

Column 3, lines 22-23, "0.1 Hz, say about 10 Hz to about 15 Hz" should read --0.1 Hz to about 15 Hz, say about 10 Hz.--

Signed and Sealed this

Fifteenth Day of December, 1987

Attest:

DONALD J. QUIGG

*Attesting Officer*　　　　　　*Commissioner of Patents and Trademarks*